US007820634B2

(12) United States Patent
Badylak et al.

(10) Patent No.: US 7,820,634 B2
(45) Date of Patent: Oct. 26, 2010

(54) COMPOSITION AND METHOD FOR PRODUCTION OF TRANSFORMED CELLS

(75) Inventors: Stephen F. Badylak, W. Lafayette, IN (US); Jeffrey Bonadio, Ann Arbor, MI (US); Sherry Voytik, Lafayette, IN (US)

(73) Assignees: Purdue Research Foundation, West Lafayette, IN (US); The Regents of the University of Michigan, Ann Arbor, MI (US); Clarian Health Partners, Inc., Indianapolis, IN (US)

( * ) Notice: Subject to any disclaimer, the term of this patent is extended or adjusted under 35 U.S.C. 154(b) by 210 days.

(21) Appl. No.: 11/799,724

(22) Filed: May 2, 2007

(65) Prior Publication Data

US 2007/0202599 A1 Aug. 30, 2007

Related U.S. Application Data

(63) Continuation of application No. 10/719,965, filed on Nov. 24, 2003, now abandoned, which is a continuation of application No. 08/390,700, filed on Feb. 17, 1995, now Pat. No. 6,653,291.

(51) Int. Cl.
*A01N 43/04* (2006.01)
*A61K 31/70* (2006.01)
*A61F 13/00* (2006.01)
*A61K 35/37* (2006.01)
*A61K 35/38* (2006.01)
*C12N 15/00* (2006.01)

(52) U.S. Cl. .................. 514/44; 424/422; 424/551; 435/455

(58) Field of Classification Search .................. 514/44
See application file for complete search history.

(56) References Cited

U.S. PATENT DOCUMENTS

| | | | |
|---|---|---|---|
| 4,902,508 A | 2/1990 | Badylak et al. | |
| 4,956,178 A | 9/1990 | Badylak et al. | |
| 5,275,826 A | 1/1994 | Badylak et al. | |
| 5,281,422 A | 1/1994 | Badylak et al. | |
| 5,352,463 A | 10/1994 | Badylak et al. | |
| 5,372,821 A | 12/1994 | Badylak et al. | |
| 5,439,446 A | 8/1995 | Barry | |
| 5,516,533 A | 5/1996 | Badylak et al. | |
| 5,554,389 A | 9/1996 | Badylak et al. | |
| 5,755,791 A | 5/1998 | Whitson et al. | |
| 5,763,416 A * | 6/1998 | Bonadio et al. | 514/44 |
| 5,962,427 A | 10/1999 | Goldstein et al. | |
| 6,653,291 B1 | 11/2003 | Badylak et al. | |
| 2005/0003537 A1 | 1/2005 | Badylak et al. | |

FOREIGN PATENT DOCUMENTS

| | | |
|---|---|---|
| WO | 92/15676 | 9/1992 |
| WO | 93/19660 | 10/1993 |
| WO | 96/25179 | 8/1996 |

OTHER PUBLICATIONS

Agrawal, S., "Antisense Oligonucleotides: Towards Clinical Trials," Reviews, TIBTECH, vol. 14, 1996, pp. 376-387.
Benvenisty, N., et al., "Direct Introduction of Genes into Rats and Expression of the Genes," Proc. Natl. Acad. Sci. USA, vol. 83, Dec. 1986, pp. 9551-9555.
Bonadio, J., et al., "Direct Gene Transfer into Skeletal Tissues in Vivo," Abstracts of Papers Presented at the 1994 Meeting on Gene Therapy, Sep. 21-25, 1994, pp. 185.
Branch, A. D., "A Good Antisense Molecule is Hard to Find," TIBS 23, Feb. 1998, pp. 45-50.
Culver, K. W., et al., "Gene Therapy for Cancer," TIG, vol. 10, No. 5, 1994, pp. 174-178.
Dubensky, T. W., et al., "Direct Transfection of Viral and Plasmid DNA into the Liver or Spleen of Mice," Proc. Natl. Acad. Sci. USA, vol. 81, Dec. 1984, pp. 7529-7533.
Gura, T., "Antisense Has Growing Pains," Research News, Science, vol. 270, Oct. 27, 1995, pp. 575-577.
Hodgson, C. P., "Advances in Vector Systems for Gene Therapy," Patent Update, Biologicals & Immunologicals, Exp. Opin. Ther. Patents, vol. 5, 1995, pp. 459-468.
Kaneda, Y., et al. "Increased Expression of DNA Cointroduced with Nuclear Protein in Adult Rat Liver," Science, Reports, Jan. 1989, pp. 375-378.
Ledley, F. D., "Pharmaceutical Approach to Somatic Gene Therapy," Pharmaceutical Research, vol. 13, No. 11, 1996, pp. 1595-1614.
Mannino R. J., et al., "Liposome Mediated Gene Transfer," BioTechniques, vol. 6, No. 7, Jul./Aug. 1988, pp. 682-690.
Marshall, E., "Gene Therapy's Growing Pains," Science, vol. 269, Aug. 25, 1995, pp. 1050-1055.
Miller, N., et al., "Targeted Vectors for Gene Therapy," The FASEB Journal, vol. 9, Feb. 1995, pp. 190-199.
Nicolau, C., et al., "In Vivo Expression of Rat Insulin After Intravenous Administration of the Liposome-Entrapped Gene for Rat Insulin I," Proc. Natl. Acad. Sci. USA, vol. 80. Feb. 1983, pp. 1068-1072.
Niyibizi, C., et al., "Potential Role for Gene Therapy in the Enhancement of Fracture Healing," Clinical Orthopaedics and Related Research, No. 355S, 1998, 5148-5153.

(Continued)

*Primary Examiner*—Anne-Marie Falk
(74) *Attorney, Agent, or Firm*—Barnes & Thornburg LLP

(57) ABSTRACT

A composition useful for the production of transformed eukaryotic cells is described. The composition comprises submucosal tissue and a nucleic acid sequence. The nucleic acid sequence is typically recombinant DNA including gene (s) encoding for one or more biofunctional proteins. The submucosal tissue component of the present composition comprises the tunica submucosa of vertebrate intestine delaminated from the tunica muscularis and at least the luminal portion of the tunica mucosa. Injection or implantation of the composition into a host induces the formation of transformed cells capable of expressing gene(s) encoded by the nucleic acid sequence.

15 Claims, No Drawings

OTHER PUBLICATIONS

Orkin, S. H., et al., "Report and Recommendations of the Panel to Assess the NIH Investment in Research on Gene Therapy," Dec. 7, 1995, 39 pages.

Seeger, C., et al., "The Cloned Genome of Ground Squirrel Hepatitis Virus is Infectious in the Animal," Proc. Natl. Acad. Sci. USA, vol. 81, Sep. 1984, pp. 5849-5852.

Stein, C. A., et al., "Antisense Oligonucleotides as Therapeutic Agents—Is the Bullet Really Magical?," Science, vol. 261, Aug. 20, 1993, pp, 1004-1012.

Verma, I. M., et al., "Gene Therapy—Promises, Problems and Prospects," Nature, vol. 389, Sep. 18, 1997, pp. 239-242.

Wolff, J. A., et al., "Conditions Affecting Direct Gene Transfer into Rodent Muscle In Vivo," BioTechniques, vol. 11, No. 4, 1991, pp. 474-485.

Wolff J. A., et al., "Direct Gene Transfer into Mouse Muscle in Vivo," Science, vol. 247, Mar. 23, 1990, pp. 1465-1468.

Wu-Pong, S., "Oligonucleotides: Opportunities for Drug Therapy and Research," Pharmaceutical Technology, vol. 18, October 1994, pp. 102-114.

Wu G. Y., et al., "Receptor-Mediated Gene Delivery and Expression in Vivo," The Journal of Biological Chemistry, vol. 263, No. 29, Oct. 15, 1988, pp. 14621-14624.

Zhu, Y. Y., et al., "Direct Gene Transfer into Regenerating Achilles' Tendon," 40th Annual Meeting, Orthopaedic Research Society, Feb. 21-24, 1994, pp. 14-3.

Zou, J.T., et al., "Characterization of a Rice Pollen-Specific Gene and Its Expression," American Journal of Botany, vol. 81, No. 5, 1994, pp. 552-561.

* cited by examiner

COMPOSITION AND METHOD FOR PRODUCTION OF TRANSFORMED CELLS

CROSS REFERENCE TO RELATED APPLICATIONS

This application is a continuation of U.S. application Ser. No. 10/719,965, filed on Nov. 24, 2003, now abandoned which is a continuation of U.S. application Ser. No. 08/390,700, filed Feb. 17, 1995, now U.S. Pat. No. 6,653,291.

GOVERNMENT RIGHTS

This invention was made with government support under Grant No. AR040679 awarded by the National Institutes of Health. The United States government has certain rights in this invention.

FIELD OF THE INVENTION

The present invention relates to the genetic transformation of cells. More particularly, this invention is directed to a method and composition for inducing the production of transformed eukaryotic cells.

BACKGROUND AND SUMMARY OF THE INVENTION

Recently much research effort has been directed to development of new procedures for introducing nucleic acid sequences into cells. One particular area of focus has been the transformation of cells forming tissues of man and other vertebrate host species to alter the phenotype of the targeted cells. For example, transformation procedures can be used to produce cells that express a biofunctional protein not endogenous to the cell or they can be used to produce cells that express elevated levels of an endogenous, but host deficient, protein. Current methods of introducing exogenous nucleic acid sequences into host tissues requires the harvesting of target cells from the host, transforming harvest cells in vitro with exogenous nucleic acid sequences, and reimplanting the transformed cells into the host.

In accordance with one embodiment of the present invention there is provided a method for introducing nucleic acid sequences into eukaryotic cells in vivo. The method comprises implanting or injecting a novel transformation composition into a host to contact tissue comprising the targeted host cells. The transformation composition comprises intestinal submucosal tissue and a nucleic acid sequence to be introduced into the targeted cell types. Compositions comprising the tunica submucosa and basilar portions of the tunica mucosa of the intestine of warm-blooded vertebrates and their use as tissue graft materials in sheet and tubular form is described in U.S. Pat. Nos. 4,902,508 and 5,281,422, which patents are expressly incorporated herein by reference. The tissue graft compositions described in those patents are used inter alia for vascular graft constructs and tendon and ligament replacement applications. Fluidized forms of intestinal submucosa are described in U.S. Pat. No. 5,275,826 issued Jan. 4, 1994, expressly incorporated herein by reference. Graft compositions comprising intestinal submucosal tissues serve as a matrix for, and apparently help to induce the regrowth of tissues replaced by or in contact with the graft constructs. The present invention is based on the discovery that delivery of exogenous nucleic acid sequences to a focal region of cellular proliferation and regeneration associated with injection or implantation of intestinal submucosal tissue, results in the production of cells containing the nucleic acid sequence and expression of proteins encoded by the nucleic acid sequence. Thus, in accordance with this invention intestinal submucosal tissue, preferably that comprising tunica submucosa and basilar portions of the tunica mucosa delaminated from adjacent tissues of vertebrate intestine, is used as an effective delivery system to introduce exogenous nucleic acid sequences into eukaryotic cells.

The terms "transformed cells" and "transformed tissues" as used herein refers to cells or groups of cells that retain their normal cell cycle, but have new or enhanced phenotypical properties deriving from the presence or expression of exogenous nucleic acid sequences introduced into the cell. The term "exogenous nucleic acid sequences" as used herein refers to any nucleic acid sequence having an origin external to the targeted cells, including recombinant nucleic acid sequences expressed in the targeted cells and/or genes not typically expressed in said cells. Genes that are capable of modifying or altering the phenotype of a cell upon introduction into the cell typically encode proteins functional in cell tissue maintenance and growth, and are generally termed herein as "biofunctional proteins".

Most present procedures for transforming eukaryotic cells rely upon indirect methods: target cells are removed from the body, infected with viral vectors carrying the new genetic information, and then reimplanted. A direct means of transforming eukaryotic cells (in vivo transformation), is preferred, but not feasible under current viral transformation procedures. Currently, retroviral vectors are the preferred vehicle for introducing DNA into eukaryotic cells. Retroviral vectors provide a high efficiency of gene transfer into replicating cells. However, the preparation of retroviral vectors requires extensive testing to ensure that no replication-competent retroviruses contaminate the vector preparation. Such extensive testing increases the cost of cell transformation procedures. In addition, even after extensive purification of retroviral vectors, the use of these vectors for human applications is still held suspect due to the association between retroviruses and cancer. An additional shortcoming of current retroviral transformation techniques is the inability to directly introduce genetic material into eukaryotic cells in vivo.

One embodiment of the present invention provides in vivo transformation of cells in a host, and thus does not require the removal and reimplantation of host tissue. Such is accomplished by use of a transformation composition including a nucleic acid sequence encoding a biofunctional protein and intestinal submucosal tissue preferably comprising the tunica submucosa, delaminated from the tunica muscularis and at least luminal portions of the tunica mucosa of vertebrate intestine. Upon implantation or injection such compositions are effective for transforming host cells and/or inducing the production of tissue comprising host cells containing and expressing exogenous nucleic acid sequences. Cells/tissues which can be targeted for transformation in accordance with this invention include musco-skeletal tissues and specifically, cells participating in the regeneration and repair of tendon, ligament, cartilage, bone and other connective tissues.

Thus, one aspect of the present invention is a composition useful for the transformation of eukaryotic cells, the composition comprising nucleic acid sequences, preferably recombinant DNA, and submucosal tissue in solid (e.g., sheet or strips) or fluidized form.

In another embodiment of this invention there is provided a method for producing transformed eukaryotic cells by contacting target cells with a transformation composition under conditions conducive to proliferation of the target cells.

Still another embodiment of the present invention is a method for inducing the formation of endogenous tissues comprising transformed cells by implanting or injecting a transformation composition, or its respective components independently, to contact tissue containing target cells in vivo.

Additional objects, features and advantage of the invention will become apparent to those skilled in the art upon consideration of the preferred embodiments exemplifying the best mode of carrying out the invention as presently perceived.

DETAIL DESCRIPTION OF THE PREFERRED EMBODIMENTS

There is provided in accordance with this invention a method and composition for producing eukaryotic cells containing exogenous nucleic acid sequences. Generally the method comprises the step of contacting target cells, in vivo with a vertebrate derived collagenous matrix and an exogenous nucleic acid sequence. Preferably those components are combined together as a transformation composition. The collagenous matrix/nucleic acid transformation compositions of the present invention can be injected or implanted into a host to induce the formation of endogenous tissues comprising transformed cells, wherein the transformed cells contain the exogenous nucleic acid sequences.

The collagenous matrix can be selected from a variety of commercially available collagen matrices or can be prepared from a wide variety of natural sources of collagen. In preferred embodiments the collagenous matrix for use in accordance with the present invention comprises highly conserved collagens, glycoproteins, proteoglycans, and glycosaminoglycans in their natural configuration and natural concentration. Most preferably the collagenous matrix comprises vertebrate submucosa-derived tissue of a warm-blooded vertebrate. This submucosal tissue can be obtained from various sources, including intestinal tissue harvested from animals raised for meat production, including, for example, pigs, cattle and sheep or other warm-blooded vertebrates.

The submucosal tissue used in accordance with the present invention is preferably derived from the intestines, more preferably the small intestine, of a warm-blooded vertebrate. Intestinal submucosal tissue typically comprises the tunica submucosa delaminated from the tunica muscularis and at least the luminal portions of the tunica mucosa. In one preferred embodiment of this invention the submucosal tissue comprises the tunica submucosa and basilar portions of the tunica mucosa including the lamina muscularis mucosa and the stratum compactum. The preparation of submucosal tissue for use in accordance with this invention is described in U.S. Pat. No. 4,902,508, the disclosure of which is expressly incorporated herein by reference. A segment of vertebrate intestine, preferably that harvested from porcine, ovine or bovine species is first subjected to abrasion using a longitudinal wiping motion to remove both the outer layers, identified as the tunica serosa and the tunica muscularis, and the innermost layer, i.e., the luminal portions of the tunica mucosa. The submucosal tissue is rinsed with saline, optionally sterilized, and it can be stored in a hydrated or dehydrated state. The use and manipulation of such tissue for the formation of ligament and tendon grafts and the use more generally of such submucosal tissue constructs for inducing growth of endogenous tissues is described and claimed in U.S. Pat. No. 5,281,422 issued Jan. 25, 1994, the disclosure of which is expressly incorporated herein by reference. It is also known that intestinal submucosal tissue can be fluidized by comminuting the tissue and optionally subjecting it to protease digestion to form a homogenous solution. The preparation of fluidized forms of intestinal submucosa is described in U.S. Pat. No. 5,275,826, the disclosure of which is expressly incorporated herein by reference. Both solid and fluidized forms of intestinal submucosa have been found, upon implantation or injection to induce endogenous remodeling processes including rapid neovascularization, proliferation of granulation mesenchymal cells, resorption of the implanted submucosa tissue and lack of immune rejection. In vivo, implanted submucosa tissue has been found effective to induce the proliferation and growth of cells/tissues with which it is in contact or which it replaces.

The nucleic acid sequence component of the present invention can include deoxyribonucleic acid (DNA) and ribonucleic acid (RNA) sequences and may encode genes that are operably linked to regulatory elements necessary for expressing the gene in a eukaryotic cell. The expression of an encoded protein is primarily directed by its promoter, although other DNA regulatory elements are necessary for efficient expression of a gene product. Promoters can be either constitutive or inducible. A constitutive promoter controls transcription of a gene at a constant rate during the life of a cell, whereas an inducible promoter's activity fluctuates as determined by the presence or absence of a specific inducer. Upon introduction into a host cell, a gene encoding sequence linked to a constitutive promoter is expressed to produce it's encoded proteins.

Alternatively the gene encoding sequence can be linked to an inducible promoter. Inducible promoters include any promoter capable of increasing the amount of gene product produced, by a given gene, in response to exposure to an inducer. Inducible promoters are known to those familiar with the art and a variety exist that could conceivably be used to drive expression of a gene. One preferred inducible promoter system for use in accordance with the present invention is the glucocorticoid system. The system consists of a gene encoding glucocorticoid receptor protein (GR) which in the presence of a steroid hormone forms a complex with the hormone. This complex then binds to a short nucleotide sequence (26 bp) named the glucocorticoid response element (GRE), and this binding activates the expression of genes linked to the GRE.

In preferred embodiments, the nucleic acid component of the present invention is a DNA sequence, and most preferably a circular DNA sequence. The circular DNA sequence can optionally include sequences allowing replication of the DNA in a bacterial cell (i.e., the nucleic acid is in the form of a plasmid). Linearized forms of DNA may likewise be used in accordance with this invention. The nucleic acid sequences of the present invention may encode biofunctional proteins that are absent or deficient in the cell or host, or they may encode proteins that facilitate cellular regeneration and repair including growth factors such as transforming growth factors, insulin growth factors, acidic or basic fibroblast growth factor, platelet derived growth factor, epidermal growth factor, hemopoietic growth factor such as interleukin 3 and the like.

Alternatively, the nucleic acid sequence component of the present invention may include an antisense nucleic acid sequence, one that is substantially complementary to at least a portion of an endogenous gene sequence, and which functions to interfere with the expression of the complimentary endogenous gene. The nucleic acid sequence component can comprise antisense mRNA itself, or can encode an antisense mRNA.

Although the submucosal tissue and the nucleic acid sequence may be used/administered separately in accordance with this invention, preferably they are combined in the form of a transformation composition. Transformation compositions in accordance with this invention useful for transformation of eukaryotic cells are prepared by combining the nucleic acid sequence with intestinal submucosa. Thus, in one embodiment of the present invention submucosal tissue in sheet or tubular form is combined by soaking the submucosal tissue in a solution comprising the nucleic acid sequences intended for delivery to eukaryotic cells. Impregnation of the submucosal constructs with the nucleic acid sequences can be enhanced by at least partially dehydrating the submucosal tissue prior to introducing it into the nucleic acid solution.

The submucosal tissue specified for use in accordance with this invention can be used in a fluidized form. Such is prepared by comminuting the submucosa by tearing, cutting, grinding, or shearing the sheet/tubes of harvested submucosa tissue. Thus pieces of intestinal submucosa can be subjected to shear in a high speed blender, or more preferably by grinding the submucosa in a frozen or freeze-dried state to produce a powder that can thereafter be hydrated with water or a buffered saline and optionally other pharmaceutically acceptable excipients to form a submucosal fluid of liquid, gel or paste-like consistency, and thereafter subjected to sterilization. The fluidized submucosa formulation can further be treated with a protease such as trypsin or pepsin at an acidic pH for a period of time sufficient to solubilize the submucosal components to provide a homogenous solution of partially solubilized submucosa which can be substituted for other fluidized forms of submucosa for use in accordance with this invention. The fluidized submucosal tissue can be blended with a solution or other source of the desired nucleic acid sequence to form a transformation composition in accordance with this invention.

The submucosal tissue of the present invention may be sterilized using conventional sterilization techniques including glutaraldehyde tanning with glutaraldehyde, formaldehyde tanning at acidic pH, propylene oxide treatment, gas plasma sterilization, gamma radiation, electron-beam and peracetic acid sterilization. A sterilization technique which does not significantly weaken the mechanical strength, structure and biotropic properties (induction of endogenous tissue repair) of the submucosal tissue is preferably used. For instance, it is believed that strong gamma radiation may cause loss of strength in the submucosal tissue. Preferred sterilization techniques include exposing the submucosal tissue to peracetic acid, 1-4 Mrads gamma irradiation, more preferably 1-2.5 Mrads of gamma irradiation and gas plasma sterilization; peracetic acid sterilization being the most preferred method. Typically, the submucosal tissue is subjected to two or more sterilization processes. After the submucosal tissue has been sterilized, the submucosal tissue may be wrapped in a plastic or foil wrap and sterilized again using electron beam or gamma irradiation sterilization techniques. Preferably the submucosal tissue is sterilized prior to combining the submucosal tissue with the nucleic acid sequence.

The transformation composition in accordance with this invention preferably comprise recombinant DNA in combination with submucosa tissue either in solid sheet or solid tube form or in fluidized form adapted for implantation or injection into a host. Such transformation compositions can be implanted or injected by methods described generally in the aforementioned and incorporated U.S. Patents describing use of intestinal submucosal tissue in sheet, tubular or fluidized form. The transformation composition can be formulated to utilize intestinal submucosa in two or more forms. For example, fluidized submucosa compositions containing a nucleic acid sequence of interest can be injected into and used as a filler for an implant and construct formed, for example, from one or more sheets of intestinal submucosa formed into sealed or sutured pouches or "pillows" for use in cosmetic, therapeutic or trauma related-surgical procedures. Thus, one transformation composition contemplated in accordance with this invention is a tissue graft construct comprising submucosal tissue formed into a sealed pouch and filled with a fluidized submucosal tissue graft composition comprising a suspension of comminuted submucosal tissue or protease digested submucosal tissue and a nucleic acid sequence. Implantation of the transformation composition promotes the proliferation and growth of the cells of tissue and contact with said implanted composition. The transformation composition is gradually resorbed and replaced with endogenous connective tissue comprising cells transformed to express the contained nucleic acid sequence.

EXAMPLE 1

Two dogs were each implanted with submucosal tissue soaked in a DNA solution to demonstrate the ability of the transformation compositions to introduce DNA sequences into cells participating in tissue regeneration. The DNA solution comprised a DNA sequence in the form of a plasmid (the pSV beta-galactosidase control plasmid, commercially available from Promega) which encodes for the beta-galactosidase protein. Beta-galactosidase is an excellent reporter enzyme that can be detected quickly by histochemical techniques utilizing the indicator compound 5-bromo-4-chloro-3-indolyl beta D galactoside (X-gal). Mammalian species do not encode beta-galactosidase naturally. The beta-galactosidase used in these experiments was of *E. coli* origin and was inserted into the pSV vector. The pSV plasmid vector is designed for use as a positive control for monitoring transformation efficiencies of mammalian cells. Procedures for utilizing this plasmid for analyzing transformation efficiencies are well known to those of ordinary skill in the art and are well accepted for establishing transformation efficiencies.

Intestinal submucosal tissue (of porcine origin) was soaked for fourteen days at 4° C. in a solution of pSV beta-galactosidase control plasmid (one milligram per ml). The soaked submucosal tissue was then implanted as an Achilles tendon graft in the hind leg of a dog. Three weeks after implantation the implanted material was harvested. The material was fixed in 0.5% glutaraldehyde in phosphate buffered saline. Standard methods were used to search for beta-galactosidase expression in the implanted material. The contralateral Achilles tendon was also harvested and fixed in 0.5% glutaraldehyde in phosphate buffered saline, to served as a control specimen. Results have shown that cells within the submucosal tissue, remodeled Achilles tendon expressed the beta-galactosidase enzyme. This expression was observed by histochemical demonstration of the beta-galactosidase enzyme activity (a blue X-gal reaction product). Beta-galactosidase activity was detected within the remodeled connective tissue structures and within adjacent connective tissues that contacted the submucosal tissue. For example, the skeletal tissue within the bone tunnel that was part of the anterior cruciate ligament replacement also expressed the protein. No beta-galactosidase activity was detected within the contralateral Achilles tendon control tissues.

An additional control experiment was also done, in which submucosal tissue alone was fixed and prepared in identical fashion to the remodeled Achilles tendon. The submucosal tissue, in the absence of exogenous DNA sequences, showed no X-gal reaction product.

EXAMPLE 2

A second experiment was done in which porcine origin intestinal submucosal tissue was used in identical fashion as in example 1. However, the pSV plasmid soaked material was used as an anterior cruciate ligament graft. Once again, the submucosal tissue was soaked for two weeks, implanted in two dogs for three weeks, then harvested. The contralateral anterior cruciate ligament (ACL) served as a control. Results were identical to the Achilles tendon study in which the submucosal implanted material showed expression of the protein in the host derived mononuclear spindle cells. The contralateral control was negative for expression of the X-gal protein reaction product.

EXAMPLE 3

A second set of two experiments was done in which the DNA plasmid vector used was BAG. The BAG vector consists of a retroviral genome within a bacterial plasmid backbone. The same two experiments as described in examples 1 and 2 (Achilles tendon and anterior cruciate ligament replacement) were performed using this alternative vector. Results were identical to those described in examples 1 and 2. That is, expression of the beta-galactosidase enzyme was detected in both locations contacted with exogenous DNA impregnated submucosal tissue, whereas the contralateral controls and the SIS alone controls were negative for expression of the protein.

The above experiments demonstrate that the production of cells containing exogenous nucleic acid sequences can be induced by contacting target cells with a transformation composition comprising intestinal submucosal and the exogenous nucleic acid sequence under conditions conducive to the proliferation of said target cells. The intestinal tissue comprises vertebrate tunica submucosa and basilar portions of the tunica submucosa. In preferred embodiments the intestinal tissue comprises the tunica submucosa delaminated from the tunica serosa and at least the luminal portions of the tunica mucosa of vertebrate intestine. Nucleic acid sequences encoding beta-galactosidase were introduced into host cells, used host cellular machinery and resulted in expression of a protein which would not otherwise be found in these tissues.

EXAMPLE 4

Numerous disease states can be treated in accordance with this invention by in vivo transformation of cells at sites of tissue regeneration and repair. These include:

1. Degenerative joint disease, as occurs in osteoarthritis, requires regeneration of articular cartilage over the surface of eburnated bone. Intestinal submucosal tissue can be utilized to induce transfer and expression of the gene for insulin-like growth factor-1, an anabolic agent for articular cartilage.

2. Soft tissue injury, as occurs in athletics (e.g., the Achilles' tendon, the cruciate and collateral ligaments of the knee, or the myotendinous junction of muscles such as the hamstring or gastrocnemius), requires regeneration/repair of injured musculo-skeletal soft tissues. The use of intestinal submucosal tissue may be combined with transfer and expression of the gene for epidermal growth factor (in the case of Achilles' tendon and cruciate ligament injury) or platelet-derived growth factor (in the case of myotendinous junction injury). Each of these growth factors has been shown to stimulate the repair process.

3. Bone fracture, as occurs with excessive trauma and with skeletal deficiency disorders such as osteogenesis imperfecta and osteoporosis, requires repair of the fracture site. The use of intestinal submucosal tissue may be combined with transfer and expression of a gene encoding a bone growth factor, such as parathyroid hormone, bone morphogenetic protein, insulin like growth factor-1, and transforming growth factor-beta.

4. Soft tissue ulceration requires regeneration of necrotic foci in the skin and stomach. Skin ulcers occur in diabetes or conditions characterized by atherosclerosis. Stomach ulcers occur in anxiety disorders. The use of intestinal submucosal tissue may be combined with transfer and expression of the gene for epidermal growth factor, platelet-derived growth factor, transforming growth factor beta, or fibroblast growth factor to stimulate the repair process and the regeneration of normal histology and function.

5. Autoimmune disorders may require surgical removal and regeneration of tissues. For example, regeneration of surgically removed synovial membranes that have been removed because of chronic inflammation, as a result of rheumatoid arthritis, can be enhanced by treatment in accordance with this invention. The use of intestinal submucosal tissue can be combined with transfer and expression of a gene for an immunosuppressive agent to thwart the destructive effects of chronic inflammation.

The invention claimed is:

1. A method for delivery of a deoxyribonucleic acid to cells of a host vertebrate species, said method comprising the step of contacting the cells in vivo with a composition comprising a collagenous matrix and an added exogenous deoxyribonucleic acid, wherein the collagenous matrix comprises submucosa tissue delaminated from both the tunica muscularis and at least the luminal portion of the tunica mucosa of warm-blooded vertebrate submucosa and wherein the deoxyribonucleic acid encodes a biofunctional protein.

2. The method of claim 1, wherein the step of contacting the cells comprises the step of implanting the composition into the host vertebrate species.

3. The method of claim 1, wherein the submucosa tissue is intestinal submucosa.

4. The method of claim 1, wherein the submucosa tissue is in an injectable form and the step of contacting the cells comprises the step of injecting the composition into the host vertebrate species.

5. The method of claim 1, wherein the collagenous matrix consists essentially of the tunica submucosa, and the basilar portion of the tunica mucosa of the intestine of a warm-blooded vertebrate.

6. The method of claim 1, wherein the collagenous matrix comprises a component selected from the group consisting of a collagen, a glycoprotein, a proteoglycan, and a glycosaminoglycan.

7. The method of claim 1, wherein the collagenous matrix is obtained from a source selected from the group consisting of porcine, bovine, and ovine species.

8. The method of claim 5 wherein the basilar portion of the tunica mucosa comprises the lamina muscularis mucosa and the stratum compactum.

9. The method of claim 1 wherein the collagenous matrix is obtained from a pig.

10. The method of claim 1 wherein the collagenous matrix is derived from intestinal tissue.

11. The method of claim 9 wherein the collagenous matrix is derived from intestinal tissue.

12. The method of claim 1 wherein the deoxyribonucleic acid comprises a plasmid.

13. The method of claim 1 wherein the deoxyribonucleic acid is a recombinant deoxyribonucleic acid.

14. The method of claim 1 wherein the submucosa tissue is in the form of a sheet.

15. The method of claim 1 wherein the submucosa tissue is in the form of strips.

* * * * *